US010633302B2

(12) United States Patent
Nadolny et al.

(10) Patent No.: US 10,633,302 B2
(45) Date of Patent: Apr. 28, 2020

(54) PROCESS FOR OLIGOMERIZATION OF BUTENE WITH DETERMINATION OF THE PROPORTION OF ACIDIC CATALYSIS

(71) Applicant: Evonik Degussa GmbH, Essen (DE)

(72) Inventors: Fabian Nadolny, Arnsberg (DE); Stephan Peitz, Oer-Erkenschwick (DE); Guido Stochniol, Haltern am See (DE); Robert Franke, Marl (DE); Felix Alscher, Dresden (DE); Cornelia Breitkopf, Dresden (DE); Wladimir Reschetilowski, Radebeul (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/509,532

(22) Filed: Jul. 12, 2019

(65) Prior Publication Data

US 2020/0031732 A1    Jan. 30, 2020

(30) Foreign Application Priority Data

Jul. 25, 2018  (EP) ..................... 18185533

(51) Int. Cl.
| | | |
|---|---|---|
| C07C 2/12 | (2006.01) |
| B01J 21/12 | (2006.01) |
| B01J 23/755 | (2006.01) |
| B01J 35/10 | (2006.01) |
| B01J 37/02 | (2006.01) |
| B01J 37/08 | (2006.01) |

(52) U.S. Cl.
CPC ................. *C07C 2/12* (2013.01); *B01J 21/12* (2013.01); *B01J 23/755* (2013.01); *B01J 35/1061* (2013.01); *B01J 37/0201* (2013.01); *B01J 37/08* (2013.01); *C07C 2529/072* (2013.01)

(58) Field of Classification Search
None
See application file for complete search history.

(56) References Cited

U.S. PATENT DOCUMENTS

| | | | |
|---|---|---|---|
| 4,855,528 A * | 8/1989 | Young ................. | B01J 29/7623 585/531 |
| 5,849,972 A | 12/1998 | Vicari et al. | |
| 7,939,597 B2 | 5/2011 | Bub et al. | |
| 8,258,249 B2 | 9/2012 | Bub et al. | |
| 8,293,941 B2 | 10/2012 | Kuppinger et al. | |
| 8,481,784 B2 | 7/2013 | Kuppinger et al. | |
| 8,524,945 B2 | 9/2013 | Stochniol et al. | |
| 8,895,683 B2 | 11/2014 | Kuppinger et al. | |
| 9,198,481 B2 | 12/2015 | Hortnagl | |
| 9,676,805 B2 | 6/2017 | Dyballa et al. | |
| 9,845,276 B2 | 12/2017 | Franke et al. | |
| 9,856,184 B2 | 1/2018 | Stochniol et al. | |
| 10,155,200 B2 | 12/2018 | Geilen et al. | |
| 10,189,755 B2 | 1/2019 | Reeker et al. | |
| 10,196,327 B2 | 2/2019 | Stochniol et al. | |
| 10,227,279 B2 | 3/2019 | Stochniol et al. | |
| 10,245,578 B2 | 4/2019 | Klasovsky et al. | |
| 2006/0276334 A1 | 12/2006 | Balduf et al. | |
| 2009/0068440 A1 | 3/2009 | Bub et al. | |
| 2016/0152527 A1* | 6/2016 | Peitz ........................ | C07C 2/10 549/313 |
| 2016/0257634 A1 | 9/2016 | Dyballa et al. | |
| 2019/0169104 A1 | 6/2019 | Fridag et al. | |
| 2019/0169105 A1 | 6/2019 | Fridag et al. | |
| 2019/0169106 A1 | 6/2019 | Fridag et al. | |

FOREIGN PATENT DOCUMENTS

| | | |
|---|---|---|
| WO | 95/14647 A1 | 6/1995 |
| WO | 2006/111415 A1 | 10/2006 |

OTHER PUBLICATIONS

Nadolny et al., Experimental and theoretical investigation of heterogeneous catalyzed oligomerization of a mixed C4 stream over modified amorphous aluminosilicates, Journal of Catalysis, Elsevier, p. 81-94,2018. (Year: 2018).*
Nadolny et al., U.S. Appl. No. 16/291,144, filed Mar. 4, 2019.
Nadolny et al., U.S. Appl. No. 16/293,702, filed Mar. 6, 2019.
Nadolny et al., U.S. Appl. No. 16/293,717, filed Mar. 6, 2019.
Nadolny et al., U.S. Appl. No. 16/293,859, filed Mar. 6, 2019.
Espinoza et al., "Catalytic Oligomerization of ethene over nickel-exhanged amorphous silica-alumina; effect of the nickel concentration," copyright 1987, Applied Catalysis, pp. 259-266 (8 pages).
European Search Report dated Jan. 14, 2019 in EP 18185533.9 (9 pages).
Hentschel et al., "Untersuchungen an Nickeloxidmischkatalysatoren," copyright Jun. 1982, Chemie Technik, pp. 313-316 (4 pages).
Wendt et al., "Structural and Catalytic Properties of NiO—Al2O3/SiO2 Catalysts for the Dimerization and ISomerization of Olefins," copyriht Jun. 1990, Chemistry of Microporous Crystals: Proceedings of the International Symposium on Chemistry of Microporous Crystals, Tokyo, Japan, Studies in Surface Science and Cataylsis. vol. 60, pp. 978-992 (15 pages).

* cited by examiner

*Primary Examiner* — Philip Y Louie
(74) *Attorney, Agent, or Firm* — Nexsen Pruet PLLC; Philip P. McCann

(57) ABSTRACT

The invention provides a process for oligomerization of n-butenes using a nickel-containing aluminosilicate catalyst to produce a product mixture whose ratio of 4,4-dimethylhexene to 3,4-dimethylhexene is determined and monitored. The invention further relates to a process for determining the ratio of the amount of the formed 4,4-dimethylhexene or of the formed 3-ethyl-2-methylpentene to the amount of the formed 3,4-dimethylhexene.

20 Claims, No Drawings

PROCESS FOR OLIGOMERIZATION OF BUTENE WITH DETERMINATION OF THE PROPORTION OF ACIDIC CATALYSIS

CROSS REFERENCE TO RELATED APPLICATIONS

This application is a 35 U.S.C. § 119 patent application which claims the benefit of European Application No. 18185533.9 filed Jul. 25, 2018, which is incorporated herein by reference in its entirety.

FIELD

The present invention relates to a process for oligomerization of n-butenes using a nickel-containing aluminosilicate catalyst to produce a product mixture whose ratio of 4,4-dimethylhexene to 3,4-dimethylhexene is determined and monitored. The invention further relates to a process for determining the ratio of the amount of the formed 4,4-dimethylhexene or of the formed 3-ethyl-2-methylpentene to the amount of the formed 3,4-dimethylhexene.

BACKGROUND

Oligomerization is generally understood as meaning the reaction of unsaturated hydrocarbons with themselves to form correspondingly longer-chain hydrocarbons, the so-called oligomers. Thus, for example, an olefin having eight carbon atoms (octene) can be formed by oligomerization of two olefins having four carbon atoms (butene). The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

In the case of the heterogeneously catalysed processes, oligomerization over acidic oligomerization catalysts has long been known. Systems employed industrially include acidic catalysts, for example zeolites or phosphoric acid, on a support. Isomeric mixtures of more or less branched olefins are obtained here. The designation acidic catalysis or acidic catalysts here describes BrØnsted acidity, i.e. the catalyst provides catalytically active protons. Often employed for non-acidic, heterogeneously catalyzed oligomerization of olefins with high dimer selectivity in the art are nickel compounds on support materials, wherein the nickel does not provide protons but rather acts as an electron pair acceptor (Lewis acid). Thus WO 95/14647 A1 describes a nickel catalyst comprising a support material consisting of the components titanium oxide and/or zirconium oxide, silicon oxide and optionally aluminium oxide for olefin oligomerization. Over these catalysts, mixtures of linear butenes are oligomerized to C8-olefins with a selectivity of below 75%. It is thought that the catalytic activity of nickel-based, heterogeneous catalysts for oligomerization of olefins is based on the interaction between nickel cations and surface aluminium atoms.

In the case of the oligomerization there are various mechanisms by which the oligomerization may proceed. These include acidic catalysis where the olefins form with the acid centre of a catalyst a carbenium ion which can react with the double bond of a further olefin, thus forming a new C—C bond. Since the carbenium ion is best stabilized at the most highly branched point of the cation, highly branched oligomers which are relevant almost exclusively for the production of fuels are formed. Oligomers having a relatively high linearity in particular are required industrially for further processing to afford chemical end products such as plasticizers or surfactants. A further mechanism is the coordinative mechanism where the first olefin bonds to the catalyst coordinatively. A further olefin can become attached there and lead to the formation of a new C—C bond and thus to the formation of an oligomer. The products of this mechanism are typically less highly branched.

SUMMARY

Compared to known oligomerization processes there is an ongoing need to develop novel process approaches which result in an improvement in conversion and/or selectivity when used in the oligomerization of olefins to afford linear products. It is accordingly an object of the present invention to provide an oligomerization process which makes it possible, with the oligomerization to achieve higher selectivities and higher conversions to more highly linear products, wherein this is monitored using certain product isomers.

It is a further object of the invention to be able to quantify the saturation of the catalyst acid centres with nickel to be able to achieve improved prediction of the suitability of a catalyst for oligomerization on a large industrial scale. It is a further object of the present invention to be able to interpret the catalytic data to identify formation processes of the catalyst and the deactivation of specific catalytic centres during the reaction. Since the oligomerization is performed as a continuous operation under elevated pressure the withdrawal of catalyst samples during operation is difficult if not impossible. For estimation of the further run time and assessment of the product spectrum to be expected it is therefore of great importance to be able to ascertain the state of the catalyst using the products formed.

The underlying object of the present invention was achieved with the process for oligomerization according to claim 1 and with the process for determining saturation according to claim 7. Preferred embodiments are specified in the subsidiary claims.

DETAILED DESCRIPTION

The process according to the invention is a process for oligomerization of n-butenes using a mesoporous, nickel-containing aluminosilicate catalyst over which a reactant stream containing the n-butenes is passed to form a product mixture, characterized in that the ratio of the amount of the formed 4,4-dimethylhexene to the amount of the formed 3,4-dimethylhexene in the product mixture is monitored and the catalyst is replaced upon exceedance of a threshold value for the ratio (amount of 4,4-dimethylhexene/amount of 3,4-dimethylhexene), wherein the threshold value for the ratio (amount of 4,4-dimethylhexene/amount of 3,4-dimethylhexene) is not more than 0.05, preferably not more than 0.01, particularly preferably not more than 0.005.

Determining the ratio comprises initially determining the amounts of the individual isomers preferably by gas chromatography and determining the ratio therefrom. To achieve a better separating efficiency the sample to be analyzed (product mixture) may be hydrogenated over a heterogeneous Pd-containing catalyst in the liner with hydrogen as the carrier gas before reaching the separating column. The alkanes obtained therefrom are more readily distinguishable than the C8 olefin isomers formed in the oligomerization.

The ratio (amount of 4,4-dimethylhexene/amount of 3,4-dimethylhexene) may be determined continuously, i.e. uninterruptedly during the running process, or discontinuously, i.e. by regular withdrawal of a sample of the product mixture from the process during operation. It is preferable when the ratio (amount of 4,4-dimethylhexene/amount of 3,4-dimethylhexene) is determined discontinuously by sample withdrawal from the product mixture carried out at regular intervals. The intervals between the regular sample withdrawals are freely choosable and depend on the plant being operated. The intervals between the sample withdrawals in the discontinuous determination of the ratio may in principle be effected in intervals of 1 to 59 minutes, 1 to 23 hours, 1 to 6 days or 1 to 20 weeks. The intervals may also vary, i.e. for example may be longer after installation of a fresh catalyst and become shorter over time.

It has been found that, surprisingly, monitoring of the ratio of 4,4-dimethylhexene to 3,4-dimethylhexene makes it possible to achieve particularly good product qualities and a higher conversion and/or a higher selectivity toward linear products upon use in the oligomerization process according to the invention. The smaller this ratio, the lower the proportion of acidic catalysis in the oligomerization and thus the lower the amount of more highly branched oligomers formed. However, if there is an increase in the ratio of 4,4-dimethylhexene to 3,4-dimethylhexene a formation has occurred on the catalyst surface. This makes it possible to determine for further operation the average degree of branching that the formed oligomers will have. If a particular threshold value is exceeded during the process the catalyst must be replaced. It is therefore possible to achieve a high linearity of the formed oligomers virtually uniformly since by establishing a suitable threshold value for the ratio the process may be prematurely interrupted and the catalyst replaced before relatively large amounts of branched byproducts are even formed.

If catalyst replacement is required due to exceedance of the threshold value the used catalyst is replaced by a fresh catalyst. Depending on the construction of the plant this proceeds in a manner known to those skilled in the art. The fresh catalyst may be a newly produced catalyst or a used but regenerated catalyst.

The reactant stream containing the n-butenes may also be a stream of pure n-butene though this is scarcely feasible industrially. Industrial mixtures containing N-butenes and employable as the reactant stream are light petroleum fractions from refineries, $C_4$ fractions from FC crackers or steam crackers, mixtures from Fischer-Tropsch syntheses, mixtures from the dehydrogenation of butanes, and mixtures formed by metathesis or from other industrial processes. Mixtures of n-butenes suitable for the process according to the invention are obtainable for example from the $C_4$ fraction of a steam cracker. Butadiene is removed in the first step here. This is accomplished either by extraction or extractive distillation of the butadiene or by selective hydrogenation thereof. In both cases a virtually butadiene-free $C_4$-cut is obtained, namely raffinate 1. In the second step, isobutene is removed from the $C_4$-stream, for example by production of methyl tert-butyl ether (MTBE). Other options include the reaction of the isobutene from the raffinate I with water to afford tert-butanol or the acid-catalysed oligomerization of isobutene to afford diisobutene. As desired, the now practically isobutene-free C4-cut, raffinate II, contains the n-butenes and possibly butanes.

In a preferred embodiment the raffinate I (butadiene-free C4 cut from the steam cracker) or raffinate II (butadiene- and isobutene-free C4 cut from the steam cracker) are supplied to the process as the reactant stream.

A further option for producing a suitable olefin mixture is that of subjecting raffinate I, raffinate II or a similarly constituted hydrocarbon mixture to hydroisomerization in a reactive column. This may afford inter alia a mixture consisting of 2-butenes, small proportions of 1-butene and possibly n-butane and also isobutane and isobutene.

Depending on the origin and workup of the reactant stream compounds comprising heteroatoms, in particular nitrogen-, sulfur- and/or oxygen-containing compounds, may be present in the stream.

The oligomerization process according to the invention is preferably carried out at a temperature in the range from 50° C. to 200° C., preferably in the range 60° C. to 180° C., particularly preferably in the range from 60° C. to 130° C. The pressure in the process according to the invention is preferably in the range from 10 to 70 bar, particularly preferably in the range from 15 to 42 bar.

In a further preferred embodiment the reactants are present in the liquid phase in the process according to the invention. If the oligomerization is to be carried out in the liquid phase the parameters pressure and temperature must to this end be established such that the reactants are in the liquid phase.

In the process according to the invention for oligomerization the weight-based space velocities (reactant mass per unit catalyst mass per unit time; weight hourly space velocity (WHSV)) are preferably in the range between 1 g of reactant per g of catalyst and per h (=1 $h^{-1}$) and 190 $h^{-1}$, preferably between 2 $h^{-1}$ and 35 $h^{-1}$, particularly preferably between 3 $h^{-1}$ and 25 $h^{-1}$.

The oligomerization catalyst used according to the invention comprises at least nickel oxide and an aluminosilicate as the support material, preferably an amorphous aluminosilicate. In the context of the present invention "amorphous" is to be understood as meaning the property of a solid which results from the fact that the solid has no crystal structure, i.e. no long-range order. However, it cannot be ruled out in the context of the present invention that the amorphous silica-alumina support material has small crystalline domains. The amorphous silica-alumina support material is not a crystalline material, for example not a zeolitic material.

The nickel-containing aluminosilicate catalyst employed in the process according to the invention is mesoporous, i.e. comprises at least mesopores. The average pore diameter of the employed aluminosilicate catalyst is preferably at least 0.7 nm. The average pore diameter may be determined by mercury porosimetry according to DIN 66133 (1993-06 version).

The nickel-containing aluminosilicate catalyst according to the invention preferably comprises nickel in an amount of 0.1% to 51% by weight, preferably 1% to 42% by weight, particularly preferably 5% to 33% by weight, based on the total composition of the mesoporous nickel-containing aluminosilicate catalyst. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium dioxide in its total composition.

According to the invention the nickel-containing aluminosilicate catalyst may have a specific surface area (calculated according to BET) of 150 to 700 $m^2/g$, preferably 190 to 600 $m^2/g$, particularly preferably of 220 to 550 $m^2/g$. The BET surface area is measured by nitrogen physisorption according to DIN ISO 9277 (2014-01 version).

In a further preferred embodiment the nickel-containing aluminosilicate catalyst has a silicon-aluminium ratio (Si/Al) of 1 to 100, preferably 2 to 80, particularly preferably 3 to 50.

Reactors that may be used and are suitable for performing the process according to the invention include reactors known to those skilled in the art in which an oligomerization may be performed continuously or discontinuously. In a preferred embodiment a fixed bed reactor or a slurry reactor in continuous or discontinuous operation is used for performing the oligomerization process according to the invention. The process is in particular performed under heterogeneous catalysis.

In a preferred embodiment the degree of dimerization (also referred to as "percentage selectivity based on dimerization") for the product/product stream obtained from the oligomerization based on the converted reactant is at least 60%, more preferably at least 75%, particularly preferably at least 80%.

The linearity of an oligomerization product/of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a $C_8$ fraction. The lower the ISO index, the more linear the construction of the molecules in the respective fraction. The ISO index is calculated by the following general formula:

$$\frac{\begin{pmatrix} \text{singly branched dimers (\% by weight)} + \\ 2 \times \text{doubly branched dimers (\% by weight)} \end{pmatrix}}{100}$$

Accordingly, a dimer mixture having an ISO index of 1.0 has an average of exactly 1 methyl branch per dimeric molecule.

The ISO index of the product from the oligomerization process according to the invention is preferably 0.8 to 1.2, more preferably 0.8 to 1.15.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a $C_9$ alcohol mixture by hydrogenation. The $C_9$ acid mixture may be used for producing lubricants or siccatives. The $C_9$ alcohol mixture is a precursor for the production of plasticizers, particularly dinonyl phthalates, or DINCH.

The present invention also further provides a process for determining the ratio of the amount of the formed 4,4-dimethylhexene or of the formed 3-ethyl-2-methylpentene to the amount of the formed 3,4-dimethylhexene, wherein the process comprises the steps of:
a) performing an oligomerization of n-butenes using a mesoporous nickel-containing aluminosilicate catalyst;
b) quantitative analysis of the product stream obtained from the oligomerization to determine the amounts of the C8 isomers, in particular n-octene, 3-methylheptene, 3,4-dimethylhexene, 4,4-dimethylhexene, 2,3-dimethylhexene and 3-ethyl-2-methylpentene, formed in the oligomerization; and c) determining the ratio of the amount of the formed 4,4-dimethylhexene or of the formed 3-ethyl-2-methylpentene to the amount of the formed 3,4-dimethylhexene, wherein the ratio is not more than 0.05, preferably not more than 0.01, particularly preferably not more than 0.005.

The oligomerization in step a) is preferably carried out at a temperature in the range from 50° C. to 200° C., preferably in the range 60° C. to 180° C., particularly preferably in the range from 60° C. to 130° C. The pressure in the oligomerization in step a) is preferably in the range from 10 to 70 bar, particularly preferably in the range from 15 to 42 bar.

In a further preferred embodiment the reactants are in the liquid phase in step a) of the method of determination according to the invention and the oligomerization is carried out in the liquid phase. If the oligomerization is to be carried out in the liquid phase the parameters pressure and temperature must to this end be established such that the reactants are in the liquid phase.

In step a) of the method of determination according to the invention the weight-based space velocities (reactant mass per unit catalyst mass per unit time; weight hourly space velocity (WHSV)) are preferably in the range between 1 g of reactant per g of catalyst and per h (=1 $h^{-1}$) and 190 $h^{-1}$, preferably between 2 $h^{-1}$ and 35 $h^{-1}$, particularly preferably between 3 $h^{-1}$ and 25 $h^{-1}$.

The inventive oligomerization catalyst for the oligomerization in step a) of the method of determination comprises at least nickel oxide and an aluminosilicate as support material, preferably an amorphous aluminosilicate. In the context of the present invention "amorphous" is to be understood as meaning the property of a solid which results from the fact that the solid has no crystal structure, i.e. no long-range order. However, it cannot be ruled out in the context of the present invention that the amorphous silica-alumina support material has small crystalline domains. The amorphous silica-alumina support material is not a crystalline material, for example not a zeolitic material.

The nickel-containing aluminosilicate employed in step a) of the process according to the invention is mesoporous, i.e. comprises at least mesopores. The average pore diameter of the employed aluminosilicate catalyst is preferably at least 0.7 nm. The average pore diameter may be determined by mercury porosimetry according to DIN 66133 (1993-06 version).

The inventive nickel-containing aluminosilicate catalyst for the oligomerization in step a) preferably comprises nickel in an amount of 0.1% to 51% by weight, preferably 1% to 42% by weight, particularly preferably 5% to 33% by weight, based on the total composition of the mesoporous nickel-containing aluminosilicate catalyst. In a particularly preferred embodiment of the present invention, the oligomerization catalyst in step a) is substantially free from titanium dioxide and/or zirconium dioxide, the oligomerization catalyst in particular comprises less than 0.5% by weight, preferably less than 0.1% by weight, particularly preferably less than 0.01% by weight, of titanium dioxide and/or zirconium dioxide in its total composition.

The nickel-containing aluminosilicate catalyst used for determining the saturation may be produced in particular by impregnation of an aluminosilicate with a solution containing a nickel salt or by coprecipitation from a single solution. In both cases this is followed by calcination of the nickel-containing aluminosilicate catalyst at at least 450° C. in an air stream or nitrogen stream or a mixture of both.

According to the invention the nickel-containing aluminosilicate catalyst for the oligomerization in step a) may have a specific surface area (calculated according to BET) of 150 to 700 m²/g, preferably 190 to 600 m²/g, particularly preferably of 220 to 550 m²/g. The BET surface area is measured by nitrogen physisorption according to DIN ISO 9277 (2014-01 version).

In a further preferred embodiment the nickel-containing aluminosilicate catalyst used for the oligomerization in step a) has a silicon-aluminium ratio (Si/Al) of 1 to 100, preferably 2 to 80, particularly preferably 3 to 50.

Reactors that may be used and are suitable for performing the determination process according to the invention include reactors known to those skilled in the art in which an oligomerization may be performed continuously or discontinuously. In a preferred embodiment a fixed bed reactor or a slurry reactor in continuous or discontinuous operation is used for performing the method of determination according to the invention. The process is in particular performed under heterogeneous catalysis.

After the oligomerization in step a) the obtained product/the obtained product stream is quantitatively analyzed for its composition, in particular for n-octene, 3-methylheptene, 3,4-dimethylhexene, 4,4-dimethylhexene, 2,3-dimethylhexene and 3-ethyl-2-methylpentene. This may be achieved using gas chromatography methods known to those skilled in the art. Further methods, known to those skilled in the art, for structural identification of eluting hydrocarbons such as IR spectroscopy or other spectroscopic methods may likewise be employed to determine the amounts of the individual isomers.

Before the products/the product stream from step a) are sent for quantitative analysis, in particular gas chromatography, in step b), the products/the product stream may subjected to a hydrogenation to achieve better separation efficiency in the analysis by gas chromatography. This may be achieved in particular using a palladium-containing catalyst. The hydrogenation may in particular also be effected using gas chromatography in the form of hydrogenolytic gas chromatography, in particular with hydrogen as the carrier gas. Hydrogenation of the injected sample drastically reduces the number of isomers to be determined. Double bond isomers are no longer distinguished here and only skeletal isomers are identified. This information is sufficient for determining the average degree of branching of the products and for determining the ratio of 4,4-dimethylhexene to 3,4-dimethylhexene. The injected sample is separated by means of a commercially available nonpolar column. The temperature program is optimized such that effective baseline separation of the octene skeletal isomers is effected. Detection is via a flame ionization detector, FID for short. Assignment of the isomers may be via the retention time of the respective pure substance under identical measurement conditions and through the use of a mass spectrometer as the detector.

When the changing of an oligomerization catalyst is to be monitored via the process according to the invention the method of determination should be calibrated beforehand. The employed catalyst must be a nickel-free aluminosilicate to determine how high the ratio of the amount of the formed 4,4-dimethylhexene or of the formed 3-ethyl-2-methylpentene to the amount of the formed 3,4-dimethylhexene is when no nickel is present (=zero value) and the oligomerization proceeds virtually exclusively by acidic catalysis. The calibration process which is performed before the inventive process for determining saturation comprises in particular the following steps:

aa) performing an oligomerization of n-butenes using a mesoporous, nickel-free aluminosilicate catalyst at different temperatures and/or loadings (different WHSV);

bb) quantitative analysis of the product stream obtained from the oligomerization to determine the amounts of the C8 isomers, in particular n-octene, 3-methylheptene, 3,4-dimethylhexene, 4,4-dimethylhexene, 2,3-dimethylhexene and 3-ethyl-2-methylpentene, formed in the oligomerization; and cc) determining the ratio of the amount of the formed 4,4-dimethylhexene or of the formed 3-ethyl-2-methylpentene to the amount of the formed 3,4-dimethylhexene.

Optionally step aa) or step a), i.e. the oligomerization of the inventive method of determination, may be performed with addition of oxygen-, sulfur- and/or nitrogen-containing compounds such as for example water, carbon monoxide, carbon dioxide, alkylamines having 1 to 5 carbon atoms, aldehydes and ketones having 1 to 6 carbon atoms, alcohols, carboxylic acids having 1 to 6 carbon atoms and ethers and esters having 1 to 8 carbon atoms and sulfides, disulfides, thioethers and/or mercaptans having 1 to 4 carbon atoms. The addition should not exceed 10 ppmw based on the elemental O, S and/or N present in the compounds. Based on the development of the product spectrum, in particular of the ratio of 4,4-dimethylhexene and 3,4-dimethylhexene, this makes it possible to identify formation and deactivation processes brought about by oxygen-, sulfur- and/or nitrogen-containing compounds or else by sintering of nickel species due to long uptimes.

These data make it possible to make predictions about the oligomerization in continuous operation. Depending on the origin of the reactant stream heteroatom-containing compounds which may be present in very small amounts in industrial reactant streams result in changes in the catalyst during the reaction which may be better predicted by the method of determination according to the invention.

EXAMPLE

Catalyst Synthesis

Employed as the catalyst was an amorphous, acidic and mesoporous aluminosilicate in the form of granulates having an average particle diameter of 1 to 2 mm, an average pore diameter of 11 nm (determined using average pore diameter and mercury porosimetry) and a pore volume of 1 g/l. This aluminosilicate (without nickel) is used for determining the product distribution of the acid catalyzed reaction of n-butenes and for calibrating the methods of determination according to the invention.

The aluminosilicate was further impregnated with an aqueous Ni(NO$_3$)$_2$ solution to introduce nickel. The impregnation employed a volume of solution just large enough to fill the pore volume. This method is known to those skilled in the art as incipient wetness impregnation. The concentration of nickel in the solution was adapted such that the incipient wetness impregnation afforded aluminosilicate catalysts having a nickel content of 1%, 6% and 14% by weight. These catalysts were subsequently calcined in a nitrogen stream at 550° C. for 10 h.

Product Distribution for the Produced Catalysts

The oligomerization of n-butenes was performed continuously in a tubular reactor with a loading (WHSV) of 7.5 g of olefins per hour per gram of catalyst. The reaction was performed at 100° C. and a pressure of 30 bar. This ensured that the reactants and the products were in the liquid phase. The output from the reactors was analyzed by gas chromatography and the proportion of individual octene isomers in the product spectrum was determined. The proportions of n-octene (n-O), 3,4-dimethylhexene (3,4-DMH) and 4,4-dimethylhexene (4,4-DMH) are summarized in table 1.

TABLE 1

Proportions of n-octene (n-O), 3,4-dimethylhexene (3,4-DMH) and 4,4-dimethylhexene (4,4-DMH) in product spectrum and ratio of 4,4-DMH to 3,4-DMH.

| Aluminosilicate | n-O | 3,4-DMH | 4,4-DMH | Ratio of 4,4-DMH to 3,4-DMH |
|---|---|---|---|---|
| without Ni | 0.0 | 26.3 | 1.7 | 0.06 |
| 1% by wt Ni | 1.8 | 13.0 | 0.3 | 0.02 |
| 6% by wt Ni | 1.9 | 9.6 | 0.1 | 0.01 |
| 14% by wt Ni | 2.9 | 5.1 | 0 | 0 |

The aim of the present process is the formation of octene isomers that are as linear as possible. The catalyst comprising 14% by weight of nickel shows the highest amount of n-octene formed and thus also the highest selectivity for the linear dimer. As the nickel proportion decreases n-butene is increasingly converted via an acid-catalyzed mechanism, thus increasing the proportion of branched products. This is also reflected in the ratio of 4,4-DMH to 3,4-DMH. The higher the proportion of acid catalysis the greater the above ratio. A ratio of less than 0.05 characterizes the onset of coordinative catalysis and the highest proportion of desired n-octene is found at a ratio less than 0.01.

The invention claimed is:

1. A process for oligomerization of n-butenes comprising:
contacting a reactant stream comprising n-butenes with a mesoporous, nickel-containing aluminosilicate catalyst to form a product mixture;
monitoring a ratio of the amount of formed 4,4-dimethylhexene to the amount of formed 3,4-dimethylhexene in the product mixture; and
replacing the catalyst with fresh catalyst when the ratio exceeds a threshold value for the ratio, wherein the threshold value for the ratio is 0.05 or less.

2. The process according to claim 1, wherein the process for oligomerization is performed at a temperature in the range from 50° C. to 200° C.

3. The process according to claim 1, wherein the process for oligomerization is performed at a pressure in the range from 10 bar to 70 bar.

4. The process according to claim 1, wherein the mesoporous nickel-containing aluminosilicate catalyst employed in the process for oligomerization contains nickel, calculated as nickel oxide NiO, in an amount of 0.1% to 51% by weight based on the total composition of the mesoporous nickel-containing aluminosilicate catalyst.

5. The process according to claim 1, wherein the mesoporous nickel-containing aluminosilicate catalyst employed in the process for oligomerization has an Si/Al ratio of 1 to 100.

6. The process according to claim 1, wherein the mesoporous nickel-containing aluminosilicate catalyst contains no titanium dioxide and/or no zirconium dioxide.

7. The process according to claim 1, wherein the process for oligomerization is performed at a temperature in the range from 60° C. to 130° C.

8. The process according to claim 1, wherein the process for oligomerization is performed at a pressure in the range from 15 bar to 42 bar.

9. The process according to claim 1, wherein the mesoporous nickel-containing aluminosilicate catalyst employed in the process for oligomerization contains nickel, calculated as nickel oxide NiO, in an amount of 1% to 42% by weight based on the total composition of the mesoporous nickel-containing aluminosilicate catalyst.

10. The process according to claim 1, wherein the mesoporous nickel-containing aluminosilicate catalyst employed in the process for oligomerization has an Si/Al ratio of 2 to 80.

11. A process for determining a ratio of an amount of formed 4,4-dimethylhexene or of formed 3-ethyl-2-methylpentene to an amount of formed 3,4-dimethylhexene, the process comprising the steps of:
a) oligomerizing a reactant stream comprising n-butenes with a mesoporous nickel-containing aluminosilicate catalyst to form a product stream comprising C8 isomers;
b) quantitative analysis of the product stream obtained from the oligomerization to determine the amounts of the C8 isomers including n-octene, 3-methylheptene, 3,4-dimethylhexene, 4,4-dimethylhexene, 2,3-dimethylhexene and 3-ethyl-2-methylpentene formed during oligomerization;
c) determining the ratio of the amount of the formed 4,4-dimethylhexene or of the formed 3-ethyl-2-methylpentene to the amount of the formed 3,4-dimethylhexene; and
d) replacing the catalyst in step a) with fresh catalyst when the ratio exceeds a threshold value for the ratio, wherein the threshold value for the ratio is 0.05 or less.

12. The process according to claim 11, wherein the oligomerization in step a) is performed at a temperature in the range from 50° C. to 200° C.

13. The process according to claim 11, wherein the oligomerization in step a) is performed at a pressure in the range from 10 bar to 70 bar.

14. The process according to claim 11, wherein the mesoporous nickel-containing aluminosilicate catalyst employed in step a) contains nickel, calculated as nickel oxide NiO, in an amount of 0.1% to 51% by weight based on the total composition of the mesoporous nickel-containing aluminosilicate catalyst.

15. The process according to claim 11, wherein the mesoporous nickel-containing aluminosilicate catalyst employed in the oligomerization in step a) has an Si/Al ratio of 1 to 100.

16. The process according to claim 11, wherein the mesoporous nickel-containing aluminosilicate catalyst in step a) contains no titanium dioxide and/or no zirconium dioxide.

17. The process according to claim 11, wherein the oligomerization is performed at a weight hourly space velocity (WHSV) of between 1 h-1 and 190 h-1.

18. The process according to claim 11, wherein the quantitative analysis in step b) is performed by gas chromatography.

19. The process according to claim 11, wherein the oligomerization in step a) is performed at a temperature in the range from 60° C. to 130° C.

20. The process according to claim 11, wherein the oligomerization in step a) is performed at a pressure in the range from 15 bar to 42 bar.

* * * * *